US011218142B2

(12) United States Patent
Govari

(10) Patent No.: US 11,218,142 B2
(45) Date of Patent: Jan. 4, 2022

(54) SIGNAL QUALITY IN A MULTIPLEXING SYSTEM BY ACTIVELY DISCONNECTING UNUSED CONNECTIONS

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 200 days.

(21) Appl. No.: 16/016,774

(22) Filed: Jun. 25, 2018

(65) Prior Publication Data

US 2019/0393869 A1  Dec. 26, 2019

(51) Int. Cl.
| A61B 18/14 | (2006.01) |
| A61B 18/00 | (2006.01) |
| H03K 17/00 | (2006.01) |
| H03K 17/14 | (2006.01) |
| A61B 5/06  | (2006.01) |

(52) U.S. Cl.
CPC ....... *H03K 17/005* (2013.01); *A61B 18/1492* (2013.01); *H03K 17/14* (2013.01); *A61B 5/062* (2013.01); *A61B 2018/00351* (2013.01); *A61B 2018/00577* (2013.01); *A61B 2018/00839* (2013.01); *A61B 2018/00875* (2013.01)

(58) Field of Classification Search
CPC ............................ H03K 17/005; A61N 1/3686
See application file for complete search history.

(56) References Cited

U.S. PATENT DOCUMENTS

| 5,391,199 A  | 2/1995  | Ben Haim     |
| 6,239,724 B1 | 5/2001  | Doron et al. |
| 6,332,089 B1 | 12/2001 | Acker et al. |
| 6,484,118 B1 | 11/2002 | Govari       |
| 6,618,612 B1 | 9/2003  | Acker et al. |

(Continued)

FOREIGN PATENT DOCUMENTS

WO        9605768 A1     2/1996

OTHER PUBLICATIONS

Vishay Siliconix: "AN 501 The DG535/536 Wideband Multiplexers Suit a Wide Variety of Applications Introduction", Aug. 3, 1999 (Aug. 3, 1999), XP055616270, Retrieved from the Internet:URL:http://www.vishay.com/docs/70608/70608, [retrieved on Aug. 28, 2019].

(Continued)

*Primary Examiner* — William J Levicky
(74) *Attorney, Agent, or Firm* — Notaro, Michalos & Zaccaria P.C.

(57) ABSTRACT

An electronic device includes a multiplexer (MUX), a switching array and logic circuitry. The MUX includes multiple input ports and an output port, and is configured to receive, via the input ports, multiple input signals, and to output, via the output port, a selected signal among the input signals. The switching array is coupled to the input ports of the MUX and is configured to receive the input signals and to connect or disconnect between each input signal and a respective input port. The logic circuitry is electrically coupled to the switching array and to the MUX, and is configured to control the switching array to connect at least the selected signal that the MUX is outputting, and to disconnect all the input signals other than the at least selected signal.

6 Claims, 2 Drawing Sheets

(56) References Cited

U.S. PATENT DOCUMENTS

| | | | |
|---|---|---|---|
| 6,690,963 B2 | 2/2004 | Ben-Haim et al. | |
| 8,456,182 B2 | 6/2013 | Bar-Tal et al. | |
| 9,351,653 B1* | 5/2016 | Harrison | A61B 5/04014 |
| 2002/0065455 A1 | 5/2002 | Ben-Haim et al. | |
| 2003/0083584 A1 | 5/2003 | Yonce | |
| 2003/0120150 A1 | 6/2003 | Govari | |
| 2003/0135127 A1 | 11/2003 | Sackner et al. | |
| 2004/0068178 A1 | 4/2004 | Govari | |
| 2005/0245970 A1* | 11/2005 | Erickson | A61N 1/3686 607/2 |
| 2007/0252713 A1* | 11/2007 | Rondoni | A61B 5/6808 340/573.5 |
| 2009/0248020 A1 | 10/2009 | Falkenstein et al. | |
| 2011/0130669 A1* | 6/2011 | Garner | A61B 5/304 600/509 |
| 2013/0066193 A1* | 3/2013 | Olson | A61B 5/063 600/424 |
| 2014/0247152 A1 | 9/2014 | Proud | |
| 2015/0091859 A1 | 4/2015 | Rosenberg et al. | |
| 2015/0141798 A1 | 5/2015 | Bar-Tal | |

OTHER PUBLICATIONS

Chuck Reynolds: "Configuring Switch Systems for Cost-Effective Testing | EE Times", Aug. 12, 2003 (Aug. 12, 2003), XP055616426, Retrieved from the Internet:URL:https://www.eetimes.com/document. asp?d oc id=1255037, [retrieved on Aug. 29, 2019].

Extended European Search Report for corresponding European patent application No. EP 19182032.3, dated Sep. 18, 2019.

* cited by examiner

SIGNAL QUALITY IN A MULTIPLEXING SYSTEM BY ACTIVELY DISCONNECTING UNUSED CONNECTIONS

FIELD OF THE INVENTION

The present invention relates generally to medical systems, and particularly to methods and systems for improving signal quality in medical systems.

BACKGROUND OF THE INVENTION

Some medical systems sense and route large numbers of electrical signals using multiple electrical leads.

For example, U.S. Patent Application Publication 2003/0135127 describes a physiological monitoring apparatus with an improved monitoring apparel worn by a monitored individual, the apparel having attached sensors for monitoring parameters reflecting pulmonary function, or parameters reflecting cardiac function. The monitoring apparatus also includes a unit for receiving data from the sensors, and for storing the data in a computer-readable medium.

U.S. Patent Application Publication 2003/0083584 describes a "leads-off indicator" for an ECG apparatus for indicating that one or more of a plurality of ECG electrodes is not properly affixed to a patient and that that obviates the need for a conventional high frequency drive signal, but instead, employs common mode input noise as a drive signal to a reference electrode such that if one of the electrodes defining an ECG vector is not properly affixed. An impedance balancing circuit is provided for developing signals allowing identification of a lose electrode when the ECG system does not utilize a right leg electrode as a reference.

SUMMARY OF THE INVENTION

An embodiment of the present invention that is described herein provides an electronic device including a multiplexer (MUX), a switching array and logic circuitry. The MUX includes multiple input ports and an output port, and is configured to receive, via the input ports, multiple input signals, and to output, via the output port, a selected signal among the input signals. The switching array is coupled to the input ports of the MUX and is configured to receive the input signals and to connect or disconnect between each input signal and a respective input port. The logic circuitry is electrically coupled to the switching array and to the MUX, and is configured to control the switching array to connect at least the selected signal that the MUX is outputting, and to disconnect all the input signals other than the at least selected signal.

In some embodiments, the switching array is configured to receive the multiple input signals via multiple respective electrical leads, each of the electrical leads contributes a respective parasitic capacitance when connected to the MUX, and, by disconnecting the input signals other than the at least selected signal, the logic circuitry is configured to reduce a total parasitic capacitance at the MUX. In other embodiments, the electronic device includes an application-specific IC (ASIC) or a field-programmable gate array (FPGA). In yet other embodiments, each of the input signals includes a signal selected from a list consisting of electrocardiogram (ECG) signals, electrogram (EGM) signals and position signals.

In an embodiment, the input signals include analog signals, and the MUX is configured to output at least the selected signal to an analog-to-digital converter. In another embodiment, the logic circuitry is configured to control which of the multiple input signals the MUX selects at a given time.

There is additionally provided, in accordance with an embodiment of the present invention, a method including, in an electronic device that includes (i) a multiplexer (MUX), which includes multiple input ports for receiving multiple input signals and an output port for outputting a selected signal among the input signals, and (ii) a switching array, which is coupled to the input ports of the MUX, controlling the switching array to connect to respective one or more of the input ports, at least the selected signal, and to disconnect all the input signals other than the at least selected signal. At least the selected signal is received via the respective input ports, and the selected signal is output via the output port.

The present invention will be more fully understood from the following detailed description of the embodiments thereof, taken together with the drawings in which:

DETAILED DESCRIPTION OF EMBODIMENTS

Overview

Embodiments of the present invention that are described hereinbelow provide improved techniques for multiplexing multiple signals, e.g., for sampling the signals by an analog-to-digital (A/D) converter.

In some embodiments, a medical system, such as an electrophysiology systems, typically acquires and routes a large number of analog signals over a large number (e.g., a hundred) of long electrical leads. In some embodiments, the system comprises an integrated circuit (IC) device, such as an application-specific IC (ASIC), which comprises a multiplexer (MUX) having multiple input ports and an output port.

In some embodiments, the MUX is configured to receive, via the input ports, multiple input signals acquired by various sensors of the electrophysiology system, and to output, via the output port, a selected signal from among the input signals. The sensors are typically coupled to the ASIC via the long electrical leads. In some embodiments, the signal selected by the MUX is sampled and converted into a digital signal by an A/D converter, and the digital signal is processed by a processor of the system.

Each electrical lead of the system may have a parasitic capacitance on the order of a few pico-farads (pF). The hundred leads described above increase the overall capacitance by two orders of magnitude. In some cases, the selected signal is distorted by the large parasitic capacitance caused by the large number of leads connected to the input ports of the MUX. The signal distortion typically reduces the quality and reliability (QR) of the processed signals, and the overall performance of the electrophysiology system.

Given the fact that only one signal is actually selected by the MUX at any given time, the disclosed techniques reduce the parasitic capacitance by disconnecting all the input signals other than the selected signal.

In some embodiments, the ASIC comprises a switching array, which is electrically coupled to the input ports of the MUX and to the electrical leads. The switching array is configured to receive the input signals, via the electrical leads, and to connect or disconnect between each input signal and the respective input port.

In some embodiments, the ASIC further comprises logic circuitry, which is electrically coupled to the switching array and the MUX. The logic circuitry is configured to control the switching array to connect at least the selected signal that the MUX is outputting, and to disconnect all the other input signals. As a result, in some embodiments only a single electrical lead, which conveys the signal that is currently selected by the MUX, is connected to the MUX at any given time. This technique reduces the level of undesired parasitic capacitance at the MUX input, and thus reduces distortion of the selected signal at the MUX output.

System Description

Figure 1:
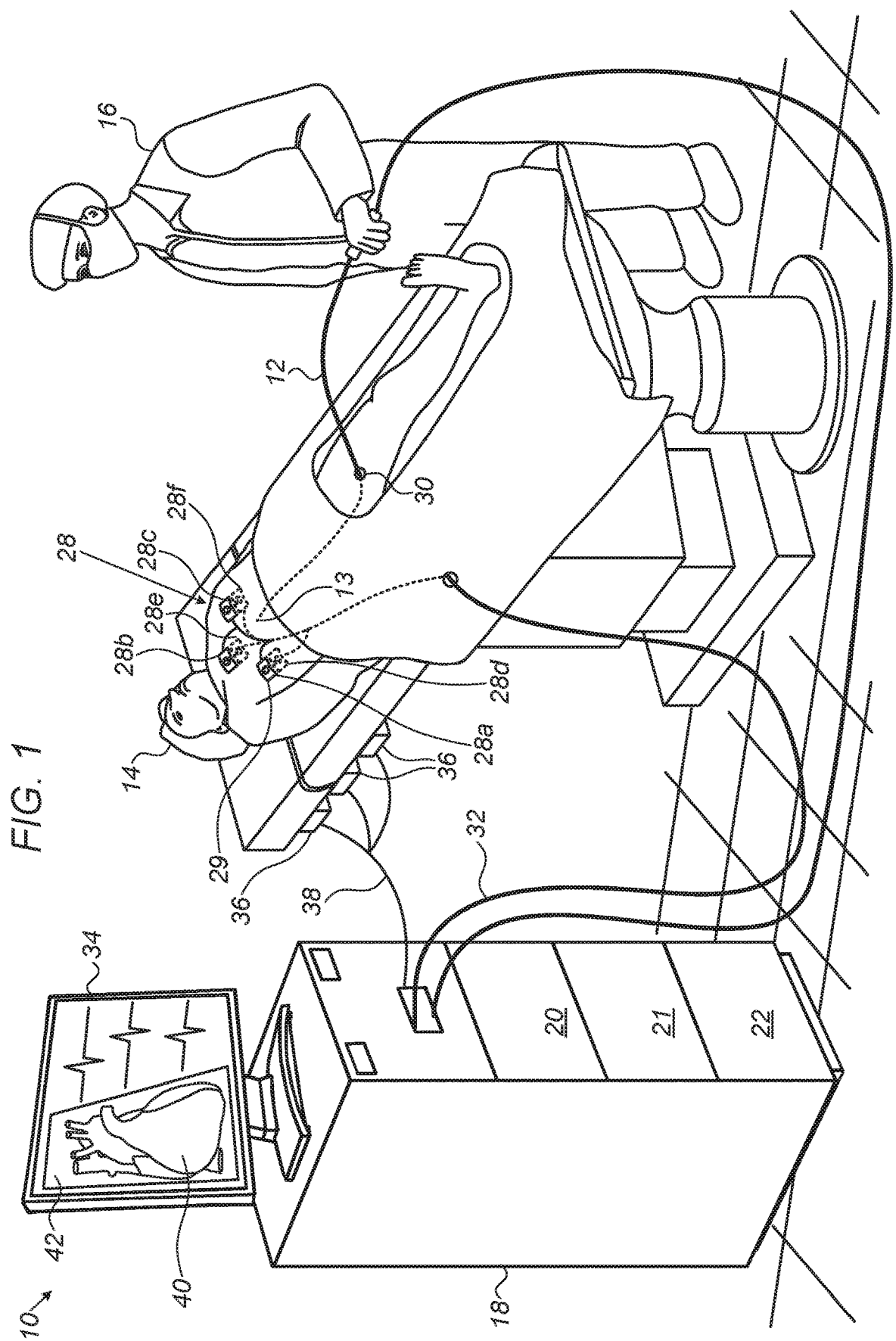
FIG. 1 is a schematic, pictorial illustration of a system for ablating tissue of a patient, in accordance with an embodiment of the present invention.

FIG. 1 is a schematic, pictorial illustration of a multiplexing medical system 10 for ablating tissue of a patient 14, in accordance with an embodiment of the present invention. The purpose of system 10 depicted in FIGS. 1 (as well as in FIG. 2 below) is to demonstrate embodiments of a multiplexing technique. The disclosed embodiments are equally applicable to any other system in which multiple signals are multiplexed to a single output.

In some embodiments, system 10 supports constructing of a mapping prior to the ablation, for mapping a heart 40 of patient 14, and using the constructed mapping, navigation of a medical tool within heart 40, during an ablation procedure, as will be described in detail below.

In some embodiments, system 10 comprises a catheter 12, comprising a distal tip 13 that comprises a plurality of devices (not shown), such as one or more ablation electrodes, one or more magnetic position sensors and an impedance sensor. In this configuration, catheter 12 with distal tip 13 is used as a calibration probe, as will be described below. During the mapping phase, (as well as during the ablation procedure), physician 16 may insert catheter 12, via an insertion point 30, into vasculature of patient 14, and may then navigate the catheter tip to the patient's heart. Subsequently, catheter 12 is used for mapping tissue of heart 40 before ablating the tissue.

In some embodiments, an operating console 18 comprises a radiofrequency (RF) generator 22, configured to generate the RF ablation signals applied by catheter 12 on the tissue of heart 40.

In some embodiments, console 18 comprises a processor 20, typically a general-purpose computer, with suitable front end and interface circuits for receiving signals from catheter 12 and for controlling the other components of system 10 described herein. Processor 20 may be programmed in software to carry out the functions that are used by the system, and the processor stores data for the software in a memory (not shown). The software may be downloaded to console 18 in electronic form, over a network, for example, or it may be provided on non-transitory tangible media, such as optical, magnetic or electronic memory media. Alternatively, some or all of the functions of processor 20 may be carried out by dedicated or programmable digital hardware components.

In some embodiments, system 10 further comprises a magnetic position tracking system, and an impedance-based active current location (ACL) system. Each of these systems may be used for tracking the position of distal tip 13 for the purpose of navigating catheter 12 to ablation locations within heart 40 of patient 14.

In some embodiments, the magnetic position tracking system comprises magnetic field-generators 36 placed at known positions external to patient 14, e.g., below the patient's torso. In an embodiment, console 18 assists in carrying out the techniques described herein.

In some embodiments, console 18 comprises a driver circuit 21, configured to drive field-generators 36 via a cable 38. When distal tip 13 is navigated by physician 16 into heart 40, the magnetic position sensor at distal tip 13, generates position signals in response to the sensed external magnetic fields produced by field-generators 36, thereby enabling processor 20 to identify the position of distal tip 13 within the cavity of heart 40.

The magnetic position sensor is connected to interface circuitry coupled to processor 20 at the catheter proximal end. In an embodiment, the position of distal tip 13 is shown on an image 42 of heart 40, which is displayed on a user display 34. In some embodiments, image 42 is acquired using an anatomical imaging system, such as a computerized tomography (CT) system or any other suitable imaging technique.

This method of magnetic-field based position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

As noted above, system 10 comprises an ACL system, which can serve as an alternative position tracking system to the magnetic-field based system. In some embodiments, the ACL system comprises a plurality of electrodes 28, which are coupled to the body of patient 14, e.g., via patches 29 that adhere to the skin of patient 14. In the example of FIG. 1, system 10 comprises six electrodes, of which electrodes 28a, 28b, and 28c are coupled to the front (e.g., chest) of patient 14, and electrodes 28d, 28e, and 28f are coupled to the back (e.g., torso) of patient 14. As shown in FIG. 1, the electrodes are arranged in pairs as follows: electrodes 28a and 28d are facing one another on the right side of patient 14, electrodes 28c and 28f are facing one another on the left side of patient 14, and electrodes 28b and 28e are facing one another on the upper part of the chest and torso of patient 14.

In other embodiments, system 10 may comprise any suitable number of electrodes, coupled to the patient skin in any suitable arrangement.

Electrodes 28 are typically connected, via a cable 32, to processor 20, which is configured to receive from the electrodes information such as values of impedance, and, based on this information, to estimate the position of distal tip 13 within heart 40 using techniques that will be described below.

In some embodiments, system 10 may comprise any other suitable sensing and/or navigation systems, such as but not limited to an electrocardiogram (ECG) system (not shown) and/or a voltage-based navigation system (not shown), in which a sensor coupled to distal tip 13 measures voltage gradient applied between external electrodes coupled to the patient torso.

Display 34 is typically configured to facilitate performance of the ablation procedure by displaying relevant information to physician 16. For example, processor 20 may register between the coordinate systems of the aforementioned tracking systems and the coordinate system of the CT system (which acquired image 42), so as to display the location and orientation of distal tip 13 within image 42, e.g., by superimposing an icon representing distal tip 13 of catheter 12 over image 42 of heart 40.

As noted above, electrodes 28 are typically used for navigating catheter 12 within the body of patient 14, using impedance-based tracking techniques, such as those described, for example, in U.S. Pat. No. 8,456,182 and US Patent Application Publication 2015/0141798, whose disclosures are incorporated herein by reference. Such techniques involve estimating the location and orientation of distal tip 13 responsively to the different impedances measured between distal tip 13 and each of electrodes 28a-28f. As described above, the estimated location of distal tip 13 may be indicated to the physician as a suitable icon on display 34. Based on this indication, physician 16 may navigate distal tip 13 of catheter 12 to one or more desired locations within heart 40.

In some embodiments, the location and orientation of distal tip 13 at any given time, are typically estimated by applying an electrical signal of a known amplitude to distal tip 13, and the resulting voltages and/or currents are measured at each pair of electrodes 28. In alternative embodiments, the electrical signal may be applied by electrodes 28, and the resulting electrical values are measured by distal tip 13.

In some embodiments, these applied electrical signals cause the pairs of electrodes 28 (e.g., pair of electrodes 28a and 28d, electrodes 28c and 28f, and electrodes 28b and 28e), each of which is located at a different position relative to the catheter, to exhibit different respective electrical values, due to a different amount of electrically-impeding tissue (and therefore, a different degree of impedance) between distal tip 13 and each of the pairs of electrodes 28.

In some embodiments, these measured electrical values are sent, via cable 32 and an integrated circuit (IC) that will be described in FIG. 2 below, to processor 20, which uses these values to estimate the relative location and orientation of distal tip 13 relative to electrodes 28 (whose positions are known). Alternatively, voltages between the distal tip of the catheter and the electrodes may be generated, and the resulting currents flowing through the electrodes may be measured and used for estimating the location and orientation of distal tip 13.

As described above, physician 16 navigates distal tip 13 to visit at multiple locations within heart 40. In some embodiments, processor 20 is configured to receive from catheter 12 at each of the visited locations, two sets of values. The first set comprises position coordinates from the magnetic position tracking system, and the second set comprises one or more respective electrical values (e.g., a value of current or impedance from each pair of electrodes 28) from the ACL system.

In some embodiments, processor 20 is configured to construct a set of data points that each comprises the position and electrical values measured at a respective position visited by distal tip 13. In some embodiments, the electrical values may be related to the position of distal tip 13. In other embodiments, electrodes coupled to distal tip 13 may acquire at some or all of the visited locations, signals related to electro-potential (EP) mapping of tissue of patient heart 40.

These sets of data points map multiple selected electrical values into respective positions, and are referred to herein as "mapping." In an embodiment, when completed, the mapping is applied (e.g., during ablation) to electrical values acquired by distal tip 13 and/or electrodes 28, for translating measured electrical values into a position measurement in heart 40. In some embodiments, a separate mapping may be constructed for selected respiration operations (for example, after a full inhalation operation, after a full exhalation operation, or a midpoint between inhalation and exhalation operations) of patient 14. In another embodiment, a separate mapping is constructed for each pair of electrodes.

In the context of the present disclosure and in the claims, the terms "position-related signals" and "position signals" are used interchangeably and refer to signals acquired by the position sensors described above. Similarly, the terms "EP-related signals" and "EP signals" are used interchangeably and refer to electrogram (EGM) and ECG signals acquired from heart 40, using various types of electrodes, such as but not limited to voltage, current, impedance and ECG sensing electrodes coupled to distal tip 13 and patches 29.

Note that the position signals and the EP signals are routed to console 18, for example, via cable 32 and catheter 12. In some embodiments, each of cable 32 and catheter 12 comprises multiple electrical leads configured to pass the signals from the sensors to console 18. Typically, each electrical lead has a parasitic capacitance on the order of a few pico-farads (pF). In some cases, a multiplexing medical system such as system 10, may comprise over a hundred electrical leads so that the cumulative total capacitance of the leads may degrade the overall system performance. For example, the parasitic capacitance may have an effect similar to a low-pass filter causing signal distortion, thereby reducing the quality and reliability of the signals. In other cases, the parasitic capacitance may cause signal latency, thereby reducing the performance of system 10.

Improving Signal Quality by Actively Disconnecting Unused Connections

Figure 2:
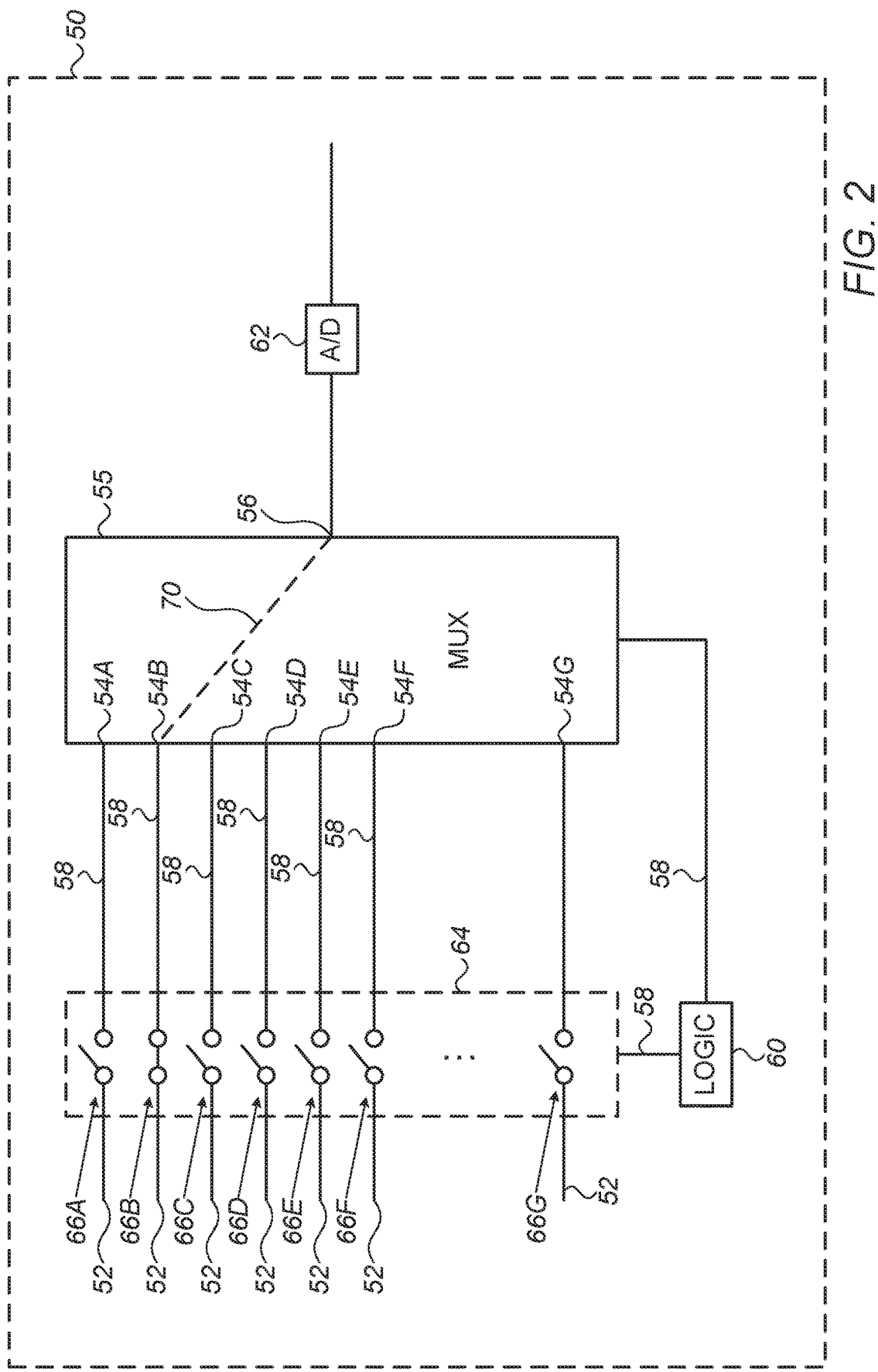
FIG. 2 is a block diagram that schematically illustrates an integrated circuit (IC), in accordance with an embodiment of the present invention.

FIG. 2 is a block diagram that schematically illustrates part of an integrated circuit (IC) 50 of console 18, in accordance with an embodiment of the present invention.

In some embodiments, IC 50 comprises a multiplexer (MUX) 55, which comprises multiple input ports 54A-54G and an output port 56. In some embodiments, MUX 55 is configured to receive, via input ports 54A-54G, multiple input signals. MUX 55 is further configured to output, via output port 56, a selected signal from among the received input signals.

In the example of FIG. 2, the signals comprise analog signals, such as the position signals and the EP signals described in FIG. 1 above. The selected signal is output via output port 56 to an analog-to-digital (A/D) converter 62, which is configured to convert the selected analog signal into a digital signal and to send the digital signal to processor 20. In a typical application, the processor receives at different time-intervals different respective digitized input signals. For example, the logic circuit may be configured to scan the input signals in a sequential cyclic order. Using such time-division multiplexing (TDM), a single processor can handle multiple different input signals.

In some embodiments, IC 50 comprises a switching array 64, which comprises switches 66A-66G coupled respectively, via electrical lines 58, to input ports 54A-54G. In the example of FIG. 2, the input signals are received via leads 52 representing, for example, the electrical leads of cable 32 and catheter 12 described in FIG. 1 above. Note that each input lead 52 corresponds to a respective switch (e.g., switch 66A) and a respective input port (e.g., port 54A). In practice, IC 50 may comprise over a hundred switches and typically the same number of input ports. As described in FIG. 1 above, the total capacitance of leads 52 may be on the order of hundreds of pF or larger.

In some embodiments, switching array 64 is configured to receive the input signals and to selectively connect or disconnect each input signal to the respective input port. By disconnecting unused input signals, the total capacitance at the input of MUX 55 reduces significantly (e.g., by a factor of 100).

In some embodiments, IC 50 further comprises logic circuitry 60, which is electrically coupled, via lines 58, to switching array 64 and to MUX 55. Logic circuitry 60 is configured to control switching array 64 to connect a single signal that is currently selected by MUX 55, and to disconnect all the other input signals received from the other electrical leads.

In alternative embodiments, logic circuitry 60 is configured to control switching array 64 to connect one or more signals in addition to the signal selected by MUX 55.

In the example of FIG. 2, at a given period of time, logic circuitry 60 controls switch 66B to connect the input signal to port 54B of MUX 55. In an embodiment, MUX 55 outputs this single input, as shown by a dashed line 70, via output port 56 to A/D device 62. Note that at the given period of time, all the other switches of array 64 disconnect leads 52 from input ports 54 of MUX 55, so that the respective input signals are not sent to the MUX.

In some embodiments, logic circuitry 60 is configured to control both MUX 55 and switching array 64. In these embodiments, circuitry 60 controls MUX 55 to select, for example, the input signal received by input port 54B, and to synchronically controls switching array 64 to connect only the input signal received by switch 66B. The logic circuitry similarly synchronizes between the selection of each input port 54 and connecting the respective switch 66.

In other embodiments, circuitry 60 controls switching array 64 to connect one or more (typically a few) input signals in addition to the input signal received by input port 54B. For example, even though MUX 55 selects only the input signal received by input port 54B, circuitry 50 may control switching array 64 to connect the input signal received by switch 66B, as well as the input signal received by switch 66A.

In alternative embodiments, logic circuitry 60 controls switching array 64 but does not choose the signal that the MUX is to select. In such embodiments, logic circuitry 60 receives, e.g., from a controller (not shown), a control signal indicative of selecting input port 54B. In these embodiments, circuitry 60 is configured to send the input to array 64 to connect only the input signal received by switch 66B. The synchronization between the control signal and the input signal may be carried out by circuitry 60 or by the controller.

By allowing, at any given time, an electrical connection between only a single lead 52 and MUX 55, the undesired capacitance experienced by MUX 55 is reduced from hundreds pF to only a few pF.

In some embodiments, the reduced level of undesired capacitance at the input of MUX 55 improves the quality and reliability of the output signal provided to A/D converter 62, and improves the overall performance of the system.

The configuration of IC 50 shown in FIG. 2 is an example configuration, which is chosen purely for the sake of conceptual clarity. In alternative embodiments, any other suitable configuration can also be used. The different elements of IC 50 may be implemented using any suitable hardware, such as in an Application-Specific Integrated Circuit (ASIC) or Field-Programmable Gate Array (FPGA). In some embodiments, some or all of the functions of IC 50 can be implemented using software, or using a combination of hardware and software elements. In some embodiments, IC 50 may further comprise any suitable volatile or non-volatile memory (not shown), e.g., a Random Access Memory (RAM) or a Flash memory.

Although the embodiments described herein mainly address cardiology systems, the methods and systems described herein can also be used in other applications, such as in any system in which multiple signals are multiplexed to a single output or to a small number of outputs.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An electronic device, comprising:
a processor;
a catheter;
a magnetic position tracking system;
logic circuitry;
a multiplexer (MUX), which comprises multiple input ports and an output port, and which is configured to receive, via the input ports, multiple input signals, and to output as an output signal, via the output port, a selected signal among the input signals, wherein the selected signal is determined by the logic circuitry controlling the MUX, the logic circuitry being electrically coupled to the MUX; and
a pre-MUX stage comprising a switching array, which is coupled to the input ports of the MUX and is configured to receive the input signals and to connect or disconnect between each input signal and a respective input port,
wherein the logic circuitry is electrically coupled to the switching array, and is configured to control the switching array to connect to the respective input port the selected signal that the MUX is outputting, and to disconnect from the respective input ports all the input signals other than the selected signal, thereby reducing parasitic capacitance at the input ports of the MUX to improve the quality and reliability of the output signal,
wherein the logic circuitry is configured to control both the MUX and the switching array,
wherein the switching array comprises a plurality of switches,
wherein each input port is coupled to one particular switch,
wherein the logic circuitry is configured to control the MUX to select the input signal received by one particular input port, and to synchronically control the switching array to connect only the input signal received by the switch coupled with that particular input port, wherein the input signals are selected from the group consisting of electrocardiogram (ECG) signals, electrogram (EGM) signals and position signals, wherein the input signals are analog signals, wherein the MUX is configured to output the selected signal to an analog-to-digital converter, wherein the processor is configured to receive from the catheter, at each location visited by the catheter, a first set of values and a second set of values, wherein the first set of values comprises position coordinates from the magnetic position tracking system, and the second set of values comprises one or more electrical values, and wherein the processor is adapted to perform time-division multiplexing, wherein the processor is adapted to receive at different time-intervals different respective digitized input signals, wherein the logic circuitry is configured to scan input signals in a sequential cyclic order.

2. The electronic device according to claim 1, wherein the switching array is configured to receive the multiple input signals via multiple respective electrical leads, wherein each of the electrical leads contributes a respective parasitic capacitance when connected to the MUX, and wherein, by disconnecting the input signals other than the selected signal, the logic circuitry is configured to reduce a total parasitic capacitance at the MUX.

3. The electronic device according to claim 1, wherein the logic circuitry is configured to control which of the multiple input signals the MUX selects at a given time.

4. A method, comprising:

in an electronic device comprising, a processor, a catheter, a magnetic position tracking system; and a multiplexer (MUX), which comprises multiple input ports for receiving multiple input signals and an output port for outputting as an output signal a selected signal among the input signals, a pre-MUX stage comprising a switching array, which is coupled to the input ports of the MUX, and logic circuitry electrically coupled to the switching array and to the MUX, controlling the switching array to connect to respective one of the input ports, the selected signal, and to disconnect all the input signals other than the selected signal, thereby reducing parasitic capacitance at the input ports of the MUX to improve the quality and reliability of the output signal; and receiving the selected signal via the respective input ports, and outputting the selected signal via the output port, wherein the logic circuitry controls the switching array, wherein the selected signal is determined by logic circuitry controlling the MUX, wherein the logic circuitry is configured to control both the MUX and the switching array, wherein the switching array comprises a plurality of switches, wherein each input port is coupled to one particular switch, wherein the logic circuitry is configured to control the MUX to select the input signal received by one particular input port, and to synchronically control the switching array to connect only the input signal received by the switch coupled with that particular input port, wherein the input signals are selected from the group consisting of electrocardiogram (ECG) signals, electrogram (EGM) signals and position signals, wherein the input signals are analog signals, and wherein the MUX is configured to output the selected signal to an analog-to-digital converter, wherein the processor is configured to receive from the catheter, at each location visited by the catheter, a first set of values and a second set of values, wherein the first set of values comprises position coordinates from the magnetic position tracking system, and the second set of values comprises one or more electrical values, and wherein the processor is adapted to perform time-division multiplexing, wherein the processor is adapted to receive at different time-intervals different respective digitized input signals, wherein the logic circuitry is configured to scan input signals in a sequential cyclic order.

5. The method according to claim 4, wherein controlling the switching array comprises receiving the multiple input signals via multiple respective electrical leads, wherein each of the electrical leads contributes a respective parasitic capacitance when connected to the MUX, and wherein, disconnecting all the input signals other than the selected signal comprises reducing a total parasitic capacitance at the MUX.

6. The method according to claim 4, wherein controlling the switching array comprises controlling which of the multiple input signals the MUX selects at a given time.

* * * * *